(12) United States Patent
Herbst

(10) Patent No.: US 7,937,683 B1
(45) Date of Patent: May 3, 2011

(54) METHOD AND APPARATUS FOR CONFIGURABLE SYSTEMS

(75) Inventor: Ewa Herbst, Edgewater, NJ (US)

(73) Assignee: Innovations Holdings, L.L.C., Pennington, NJ (US)

(*) Notice: Subject to any disclaimer, the term of this patent is extended or adjusted under 35 U.S.C. 154(b) by 472 days.

(21) Appl. No.: 12/113,200

(22) Filed: Apr. 30, 2008

Related U.S. Application Data

(60) Provisional application No. 60/926,954, filed on Apr. 30, 2007.

(51) Int. Cl.
*G06F 17/50* (2006.01)

(52) U.S. Cl. .......................... 716/138; 716/139

(58) Field of Classification Search .......... 716/116–117, 716/126–128, 138–139
See application file for complete search history.

(56) References Cited

U.S. PATENT DOCUMENTS

2009/0094570 A1* 4/2009 Artyomov et al. .............. 716/12
* cited by examiner

*Primary Examiner* — Paul Dinh
(74) *Attorney, Agent, or Firm* — Byrne Poh LLP

(57) ABSTRACT

A configurable semiconductor chip module system has analog elements, digital elements, and connection elements between the analog and digital elements. Ones of the analog and digital elements receive inputs from respective sources, and ones of said analog and digital elements output signals for generating control signals having selected electrical and time spatial properties. The connection elements are configurable after creation of the analog elements, the digital elements, and the connection elements. A method of the invention for manufacturing a flexibly configurable semiconductor single chip module for receiving and outputting various signals not specifically known at the time of manufacture; manufactures a plurality of analog elements, digital elements, and connection elements between said analog and digital elements; enables ones of the analog and digital elements for receiving inputs from respective sources, ones of the analog and digital elements for outputting signals for controlling control signals having selected electrical and time spatial properties; and configures the connections elements after creation of the analog elements, the digital elements, and connection elements, to configure the module.

18 Claims, 11 Drawing Sheets

- High Impedance Amplifier
  - Probe Types (High Impedance)
    - Ion Selective Electrode: H+ (pH), Ca++, K+, Na+, Li+, $CO_2^F-$, Cl- $NH_4^+$
    - Conductivity, Dissolved Oxygen
    - Glucose
    - Blood Gases
  - Specialty: Input resistance $>10^{15} \Omega$ Apps: Electrochemical

- Differential Amplifier
  - Probes:
    - Thermocouple, RTD, Thermistor
    - Electrodes
  - Specialty: CJC compensation, Temperature control

- BioAmplifier
  - Electrodes: EMG, EKG, EEG
  - Biopotential Electrode
  - Electrodes: Cell potential
  - Specialty: Selectable Notch, Low Pass, High Pass Filtering with Differential and Isolation Amps, some provide excitation

- Wheatstone Bridge Amplifier
  - Probes Types
    - Strain Gauge
    - Displacement Transducer
    - Pressure/differential pressure Transducer
      - Air Flow, $O_2$ Flow, BP
    - Temperature Transducer
    - Glucose
  - Specialty: Provide controlled AC/DC Excitation
  - Measurements: Blood Pressure, Glucose,

- Transimpedance Amplifier
  - Probes Types
    - Optical: Photodiodes, pH, Phosphorescence
    - Fluorescence
    - Radioactive
    - Current to voltage
  - Specialty: Provides excitation light
  - Glucose, pH,

Fig. 7

- Ultrasound Amplifier
  - Transducer Types
    - Fluid dynamics: blood velocity
    - Intravascilular
  - Generate sound waves and measure reflection
  - Blood Flow
- Audio
- Instrumentation Amplifier
  - Transducer Types
    - Thermocouple
    - Blood Transducer
    - Bridge Amplifier
    - Hall Effect Sensors
  - Arterial Blood Partial Pressure: CO, $CO_2$, $N_2$, $O_2$
  - Peroxide $H_2O_2$ Biosensor
- Differential Amplifier
  - Transducer Types
    - Thermocouple, Thermistor
  - CJC compensation
- Isolation Amplifier
  - Transducer Types
    - Thermocouple
  - CJC compensation

Fig. 8

System Specifications

Sensor Inputs and Signal Conditioning

Sensor Interface Module — Unlimited different modules

Sensor Interface Module Channels:
- 8 Differential per chip
- 16 Single ended per chip Sensor Interface Modules
- High Impedance
- Differential
- Transimpedance
- BioAmp
- Bridge
- Ultrasound
- Instrumentation
- Isolation
- General Purpose ADC—Analog and Digital — 12 to 24 bits, Precision Bipolar, Unipolar options

Power
Core: 1.8V
I/O Tolerance: 3.3V

PLL/Clock
40MHz

Communications
USB
RS232/SPI/I2C
Ethernet
SERDES

Remote

---

System Specifications

Outputs

Electrical Stimulator Module — 2 Differential
Electrical Stimulator Module Channels: +/-10V
Electrical Stimulator Vmax — 12-24 bits
DAC- Digital to Analog Conversion — 12-16 bits
MDAC-Multiplying Digital to Analog Conversion Power Stage V — +/-50V
Power Stage I — +/-300mA

RFID

Fig. 10A

Other - Input sensors

- DNA
- Lab on a chip
- Quantum dot bio probes
- Cell/protein amplifier
- Hydrogels
- Biochemical
- Nanobiomaterials
- Nanobioelectronics= Biomaterial + Nanomaterial (or metal)
- Nanomaterial=carbon nanotubes, nanoparticles, nanofibers,
- Biomaterial=enzymes, antigens,DNA
- Biopolymers
- Bacteria
- Electrode Array

Other - outputs to support

- Nanomotors
- Nanotransporter
- Stimulus
- Drug delivery

Fig 10B

METHOD AND APPARATUS FOR CONFIGURABLE SYSTEMS

CROSS-REFERENCE TO RELATED APPLICATIONS

The invention relates to a flexible analog/digital configuration, preferably on a single silicon or other semi-conductor chip for use in receiving various inputs, processing them, and being able to provide in response an electrical stimuli or control signal which can be generated, for example, by a multi-functional electric stimulator output such as those described in U.S. Pat. Nos. 6,029,090, 6,684,106, and U.S. patent application Ser. No. 11/213,050, all identifying Ewa Herbst as the inventor, the patents and patent application being incorporated herein by reference, in their entirety. This application claims the benefit of and priority under 35 U.S.C. §119(e) to U.S. Provisional Patent Application No. 60/926,954, filed Apr. 30, 2007, which is hereby incorporated by reference herein in its entirety.

BACKGROUND OF THE INVENTION

1. Field of the Invention

The invention relates generally to a flexible analog/digital configuration, the system being preferably on a chip, and used for receiving various inputs, processing them, and being able to display/communicate the results and/or provide a response thereto.

2. Status of Prior Art

Semiconductor manufacturing technology has progressed substantially to allow more custom definitions of systems on a single chip. Nevertheless, researchers in many fields, including, without limitation, biological and medical sciences, and physiotherapy, and clinicians who make use of electrical stimulators and sensors for activities in which they engage, seek further instrumentation which enables them to treat patients with specialized and customizable equipment, but at a reasonable cost, in conformance, for example, with medical insurance industry guidelines. Such equipment, while often available at high price and for specialized purposes, often does not meet the needs of these workers. As a result, those working in these and other fields of endeavor are limited in their ability to quickly react to and provide for either patient use or experimental use systems meeting their needs. Further, by "patient", we mean, as used in its broadest sense, human and non-human mammals and other animals, as well as plants (i.e. multicellular organisms).

Accordingly, it is desirable to find a method and apparatus to enable such workers to quickly generate and use systems meeting their electrical stimulation and input receiving needs without undue delay or cost. In addition, such systems need to be able to be produced as both one of a kind systems, as well as in production quantities in order to satisfy current needs.

SUMMARY OF INVENTION

In one aspect, a configurable semiconductor chip module system has analog elements, digital elements, and connection elements between the analog and digital elements. Ones of the analog and digital elements receive inputs from respective sources, and ones of the analog and digital elements output signals for generating control signals having selected electrical and time spatial properties. The connection elements are configurable after creation of the analog elements, the digital elements, and the connection elements.

In another aspect, a configurable semiconductor single chip module for use in patient treatment has analog elements, digital elements, and connection elements between the analog and digital elements. Ones of the digital and analog elements receive analog inputs from respective sources, and ones of the digital and analog elements output signals for controlling control signals having selected electrical and time spatial properties useful in medical treatment. The connection elements are configurable after creation of the analog elements, the digital elements, and the connection elements.

In a further aspect, a passive (that is, without feedback) configurable semiconductor single chip module for use in making analytical measurements of parameters related to patients' status has analog elements, digital elements, and connection elements between the analog and digital elements. Ones of the analog and digital elements receive analog inputs from respective analog sensors, and ones of the analog and digital elements output signals relating to measurements from the sensors. The connection elements are configurable after creation of the analog elements, the digital elements, and the connection elements.

A method of the invention for manufacturing a flexibly configurable semiconductor single chip module for receiving and outputting various signals not specifically known at the time of manufacture; manufactures a plurality of analog elements, digital elements, and connection elements between said analog and digital elements; enables ones of the analog and digital elements for receiving inputs from respective sources, ones of the analog and digital elements for outputting signals for controlling control signals having selected electrical and time spatial properties; and configures the connection elements after creation of the analog elements, the digital elements, and connection elements, to configure the module.

BRIEF DESCRIPTION OF DRAWINGS

Various objects, features and advantages of the present invention can be more fully appreciated with reference to the following detailed description of the invention when considered in connection with the following drawings, in which like reference numbers identify like elements:

FIGS. 7 and 8 are charts illustrating various flexibilities available in constructing elements described herein in accordance with an embodiment of the invention.

FIGS. 10A and 10B illustrate a typical system specification for various elements of a system for enabling operation of a module and its manufacturing construction, in accordance with the embodiments of the invention.

DETAILED DESCRIPTION

Figure 1:
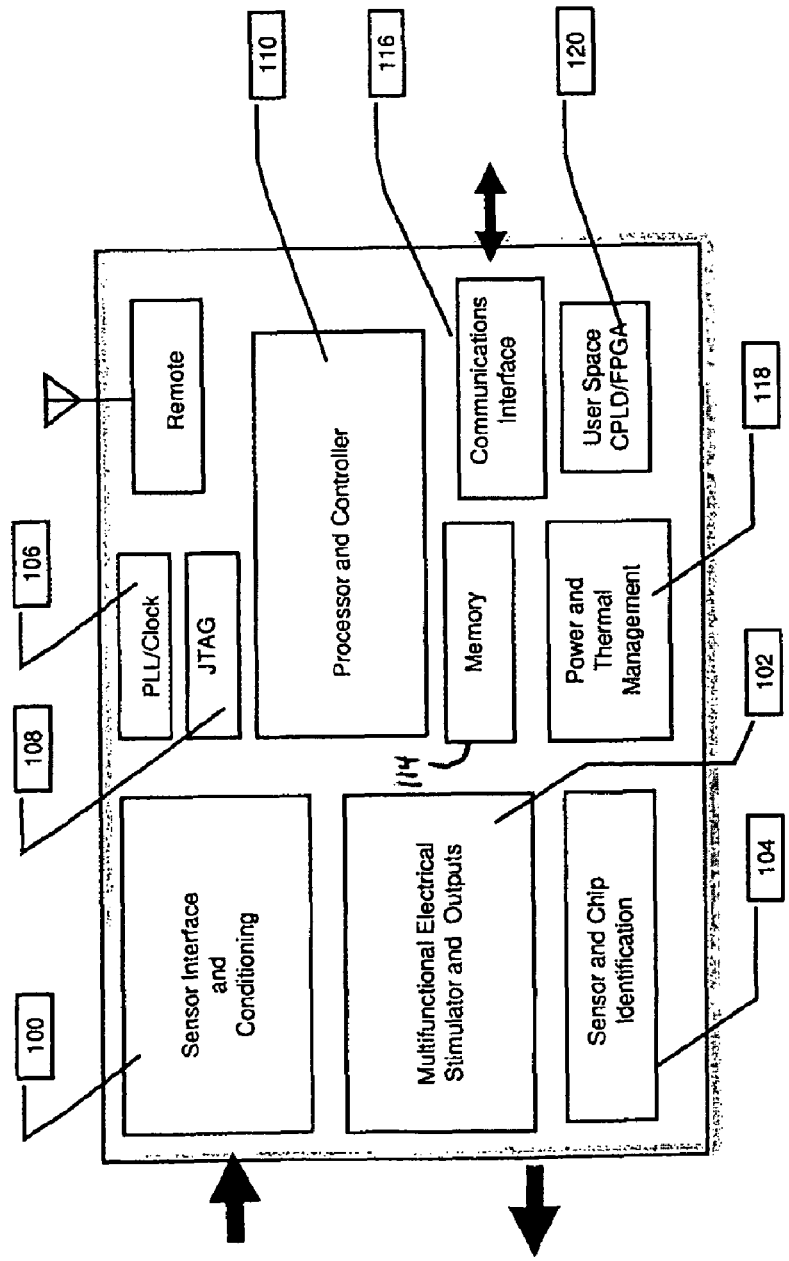
FIG. 1. describes a general block functionality in accordance with embodiments of the present invention.

The general block functionality of an embodiment of the invention is illustrated in FIG. 1. Referring to FIG. 1, the system includes a sensor interface and conditioning module 100, a multi-functional electrical simulator and output module 102, a sensor and chip identification module 104, a phase-lock loop clocking module 106, a JTAG module 108, a processor and controller module 110, a memory module 114, a communications interface module 116, a power and thermal management module 118, and a user-programmable module 120, which can be implemented as CPLD/FPGA. These elements are designed in particular to be incorporated on a single chip such as a configurable application specific standard product (ASSP) which has for example a plurality of fixed layers, on top of which several layers can be placed to customize the chip and to allow interconnections as desired between elements or modules in the fixed layers. Thus, for example, elements 100-118 might be the fixed elements on the chip and the user space would be several layers on top of the fixed layers to effect connections, additional elements needed for the chip, etc. Other chip or multichip configurations could be used as semiconductor manufacturing methods are developed or to minimize the manufacturing cost, for example, separating analog and digital functions between two chips. Further, the layers can be fixed with programmability features as known in the field.

A "system on a chip" (SoC) advantageously can measure multiple parameters; and when properly programmed, can easily organize the data from multiple sensors or other analog or digital sources. It can present or display different, or similar, pages for setting up each measurement (or each measured parameter), for example by sensor, class of sensors, etc., to enable an easy to use approach for non-technical individuals without needing to know the specifics as to many parameters. This user-friendly, and lower-cost approach further enables the measurement and interconnection to be performed using a configurable standard basic chip according to the invention.

Figure 2:
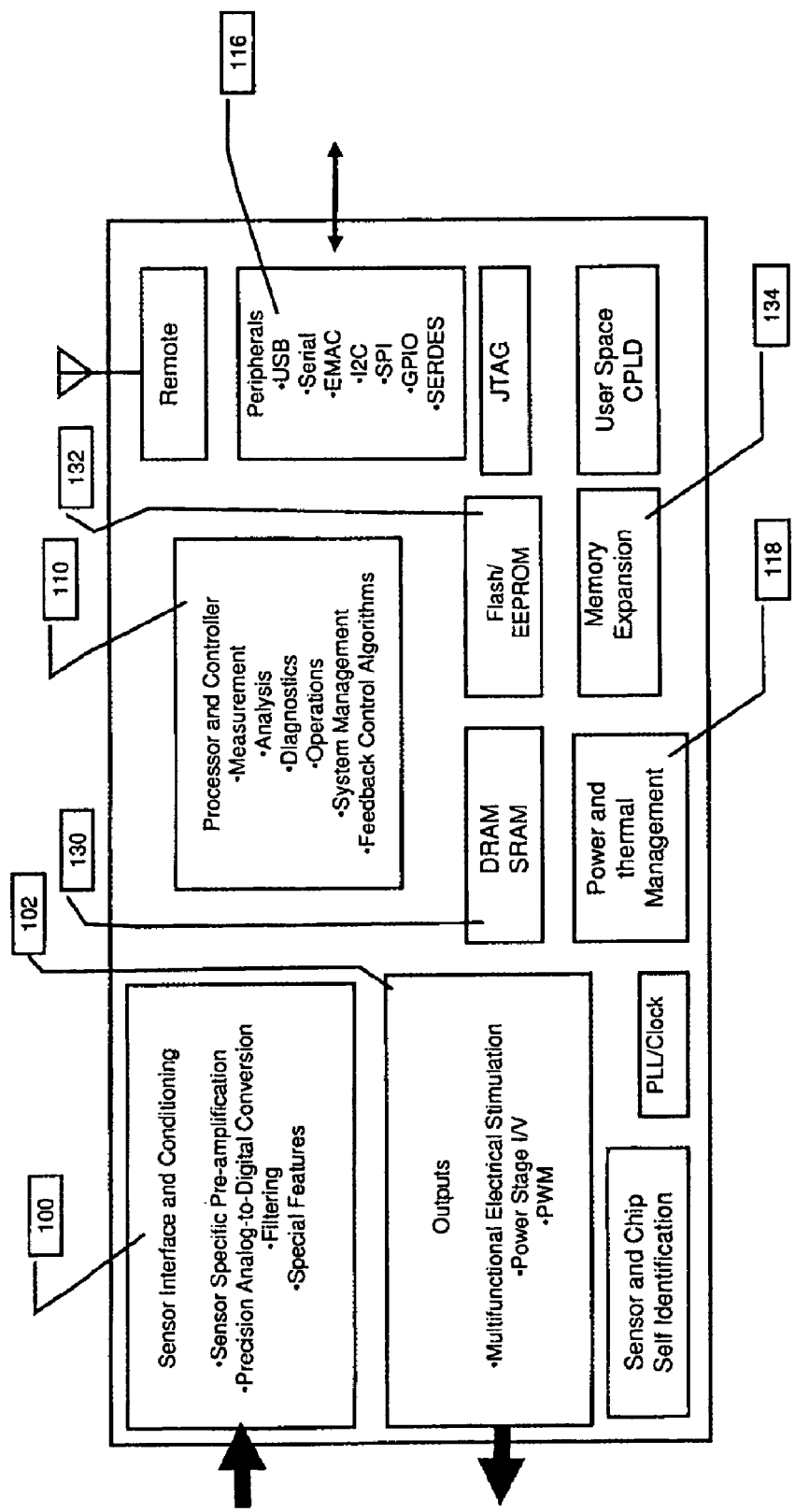
FIG. 2 illustrates a more detailed view of the general block functionality in accordance with one embodiment of the invention.

Considering the modules of FIG. 1 in more detail, and referring now to FIG. 2, the sensor interface and conditioning module 100 can include sensor-specific preamplifiers, precision analog-to-digital conversion circuitry, filters for filtering the signal inputs, and other special features depending upon the particular application to which the circuit is put. And, as described in more detail below, various components can be connected to be grouped as a family, for example by sensor functionality or characteristic, such as impedance, signal levels, etc., to more efficiently connect the analog and digital elements of the modules, in a chip layer, or between chip layers. This can also result in a smaller chip/module footprint.

The processor and controller module 110 is thus programmable by the user and/or configurable in hardware to perform the functions of measurement, analysis, diagnostics, operations, and system management, and to enable feedback control algorithms as required. Each of these functions can be the subject of software applications which are stored in memory 114 (FIG. 1). Memory 114, in some embodiments, includes a DRAM and/or SRAM module 130, a flash or EE PROM memory 132 and can have available space for memory expansion 134 (FIG. 2). The multi-functional electrical stimulator and output module 102, in addition to providing a multi-functional electrical stimulation unit, such as that described in the Herbst patents and patent application identified above, can also provide a power stage for controlling current and voltage as well as a pulse width modulator stage (PWM) for effecting the outputs of the module 102. Furthermore, the communications interface 116 can communicate to various peripherals using video, audio, or any of a number of protocols, all of which can be supported by a suitable design on the chip. Those protocols can include, for example, USB, Ethernet, I2C, SPI, GPIO, and SERDES protocols. Other protocols, as they are developed or as they are required by the user, could also be either preprogrammed into the hardware or programmed into the software depending upon the particular design of the chip or chip set. Further the "peripherals" can include servers and server interfaces, and functions of the electrostimulator module, for example, power, sensing/sensors, feedback controls, and protocol conversions.

Figure 3:
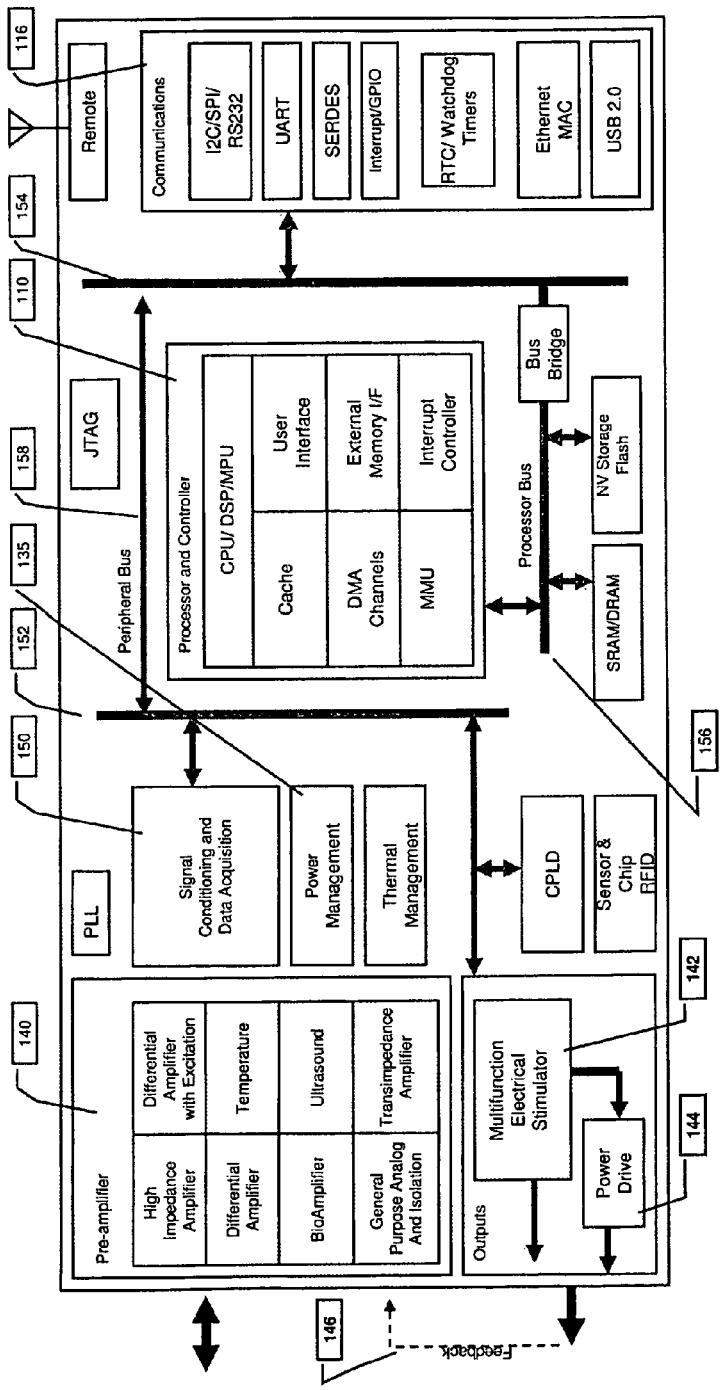
FIG. 3 illustrates in more block level detail, an embodiment of elements of the system on a chip and details as to the acronyms relating to various of the elements.

Referring now to FIG. 3, which illustrates in more block level detail one embodiment of the elements of a system on a chip and which provides detail as to the acronyms related to various of the elements, the sensor interface and conditioning module preamplifier section 140 can include any (or all) of a number of amplifier types such as a high impedance amplifier, a differential amplifier with or without excitation, a temperature amplifier, a bioamplifier, an ultrasound amplifier, a transimpedance amplifier, and generally a general purpose analog amplifier with or without isolation.

The multi-functional electrical stimulation and output module 102 can have in particular an output section which enables the multi-functional electrical stimulator 142 in a manner comparable to that described in the patents identified above to generate output signals in response to instructions or control signals from the processor and/or controller, the signal conditioning and data acquisition module, or the user-programmable module. The output of the multi-functional electrical stimulator can be provided directly to output receiving elements (not shown) or through an amplifier or power drive 144 to such receiving elements. In a particular embodiment, outputs from the output module can be fed back (146) as an input to the sensor interface and conditioning module 100 through a separate process to help provide closed-loop control of the output stimulation signals. The output module 102 can also be used to generate desired output signals in response to, for example, user programming.

The signal conditioning in data acquisition portions 150 of the sensor interface and conditioning module 100 connect to a first bus 152 which in some embodiments connects also to a peripheral bus 154.

The processor and controller module 110, referring to FIG. 3, is further broken down to show various elements of the module 110. The module may include many of the "standard" elements of a standard processor including the CPU or digital signal processing element or multiple processing unit, cache, a user interface module, a direct memory access (DMA) channel or channels, a memory management unit (MMU), an interrupt controller, and an external memory interface. These can be connected through a processor bus 156 to various portions of the memory, such as SRAM, DRAM or the non volatile (NV) storage flash memory. In the illustrated embodiment, the processor and controller module 110 has two processor bus elements 156 and 158 which connect to bus 154. The communications interface module 116 connects to bus 154. As illustrated, the communications module can have, in addition to the elements identified in connection with FIG. 2, a UART, an interrupt/GPIO, an RTC/Watchdog timer, an Ethernet MAC, an optical peripheral device, and the USB protocol identified in FIG. 3 as USB 2.0. FIG. 3 also sets forth many of the acronyms used in the figure for convenience.

Figure 4:
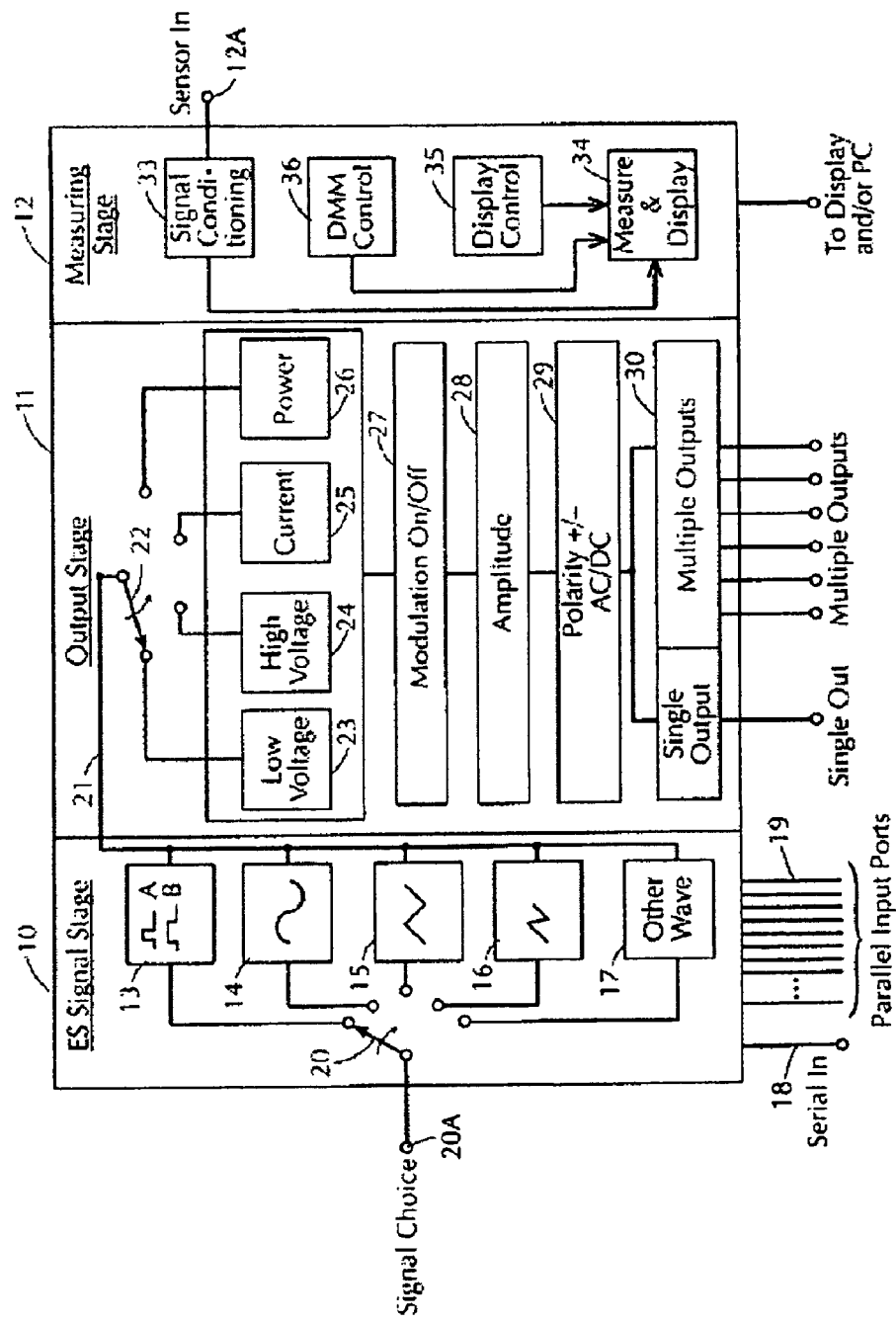
FIG. 4 illustrates a multifunctional stimulator in greater detail.

Referring now to FIG. 4, the multi-functional stimulator is shown in greater detail with reference to the multi-functional stimulator described in the above-identified patents. The reader is referred to, for example, U.S. Pat. No. 6,029,090 for a more complete and detailed description and understanding of the various elements described in FIG. 4 and which would correspond substantially to portions of module 102, referring to FIG. 1.

Figure 5:
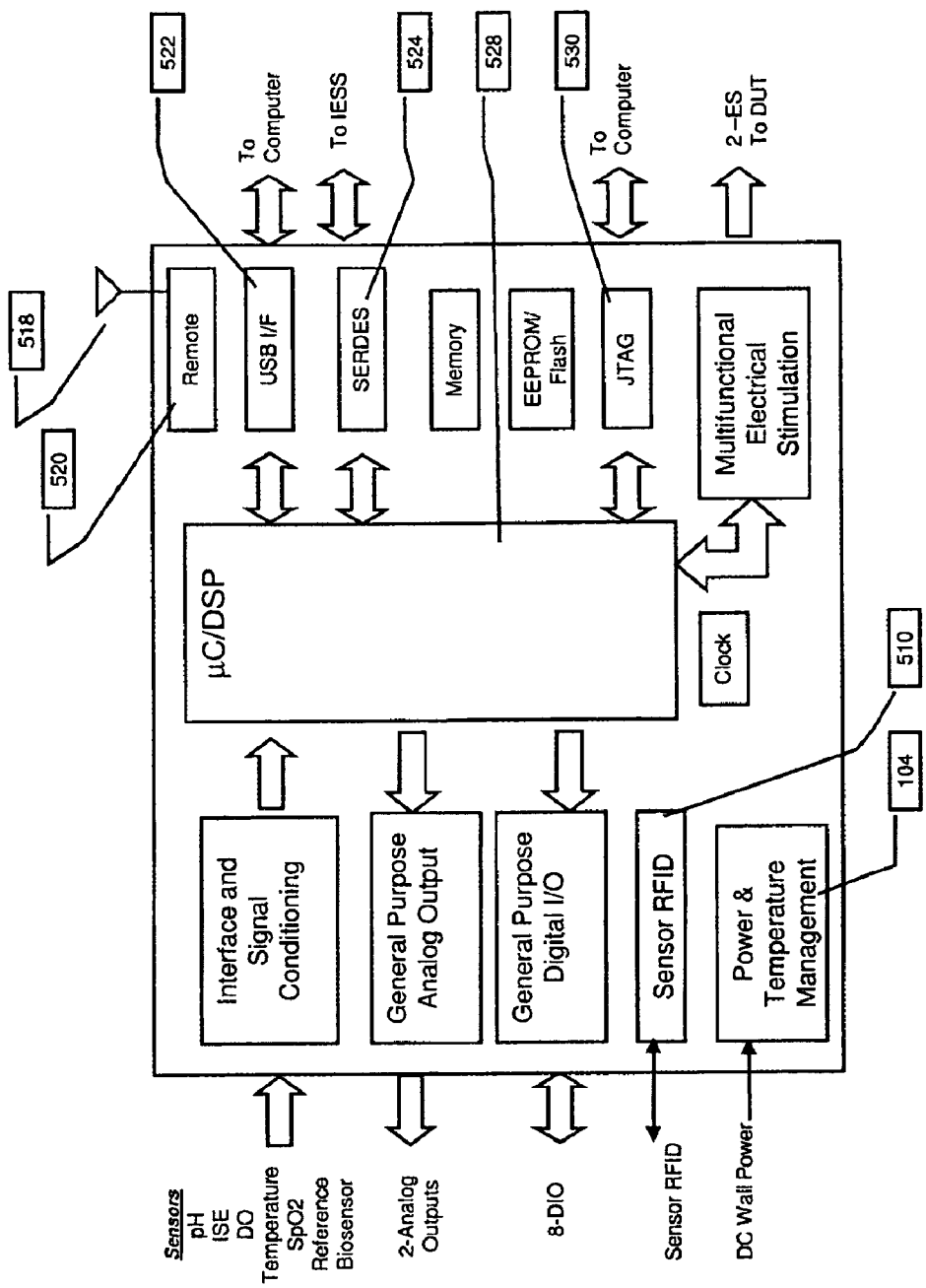
FIG. 5 illustrates a particular implementation of the system on the chip in accordance with an embodiment of the invention.

Referring now to FIG. 5, there is illustrated a particular embodiment of the system showing the general interconnection and operation of the various components, and including some specificity with regard to the sensors which might be connected to the interface and signal conditioning, the ability to provide two analog outputs and eight digital outputs, as an example, the use of a sensor RFID module 510, and using the power and temperature management module 104 across the chip. On the other side of the chip or module, the ability to wirelessly connect to the module through antenna 518 and remote sending and receiving module 520 is illustrated. Alternatively, a computer can be connected to the module through USB IF (USB interface) element 522. Other interface connecting signals in this illustrated embodiment are provided through the serial deserializer 524. The multi-functional electrical stimulator is illustrated as being controlled by the microcontroller or DSP 528 and provides outputs as illustrated. The JTAG module 530 for example, connects also to the microcontroller as well as to an external computer.

Figure 6:
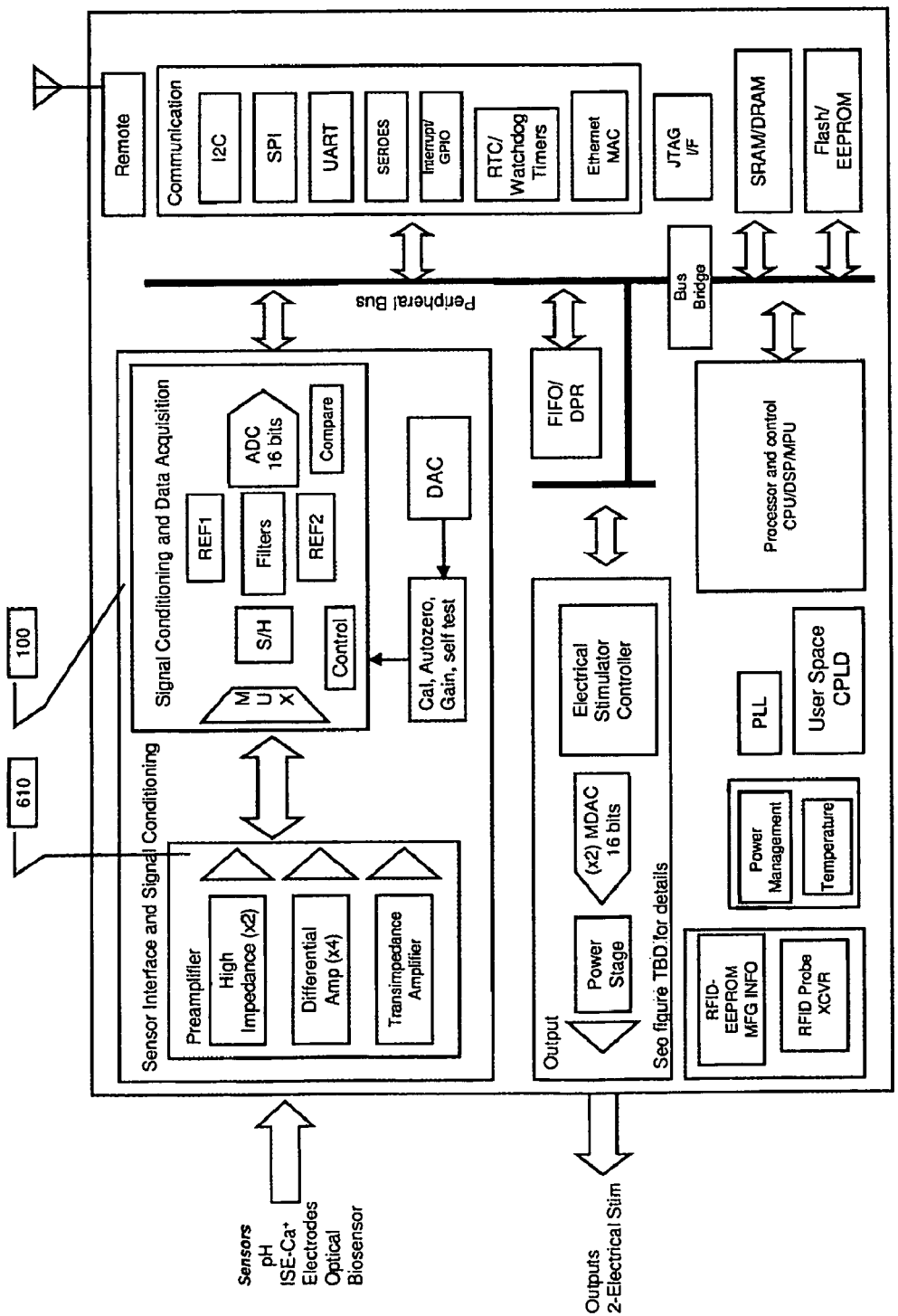
FIG. 6 illustrates details regarding an exemplary sensor interface and conditioning module.

Referring now to FIG. 6, further detail is provided with regard to an exemplary sensor interface and conditioning module 100. As illustrated, different sensors can be provided and treated differently by the high impedance, differential, and transimpedance amplifiers provided in the pre-amplifier module 610. The output of the pre-amplification is sent in some embodiments to the signal conditioning and data acquisition module where it can be multiplexed, sampled, filtered, and converted to a digital value as illustrated, typically, in that module. Various calibration controls are available as illustrated.

The output section contains the electrical controller mentioned above. Various digital to analog converters, here 16 bit DACs, are provided, the output of which is presented to an output stage capable of driving one or more electrical stimulation outputs. Other components illustrated in FIG. 6 are noted and are similar to, if not identical to, the related elements in FIG. 5. The charts in FIGS. 7 and 8, illustrate various flexibilities available in constructing any of the elements hereinbefore. This flexibility provides not only for a very useful and "burnable" circuitry over time, but in addition enables the user to substantially design how the system will work. In that respect, therefore, the elements of FIG. 6, representing the chip level layer, provide, for these embodiments of the invention, a particularly advantageous methodology for building the chip containing the elements and modules described herein. Thus the modules/functions can be configured by the user (for example who may not need to be technically trained) in response to needed application parameters or as a result of available classes or types of sensors/inputs to create a customized chip; that is, a chip having user-selected chip functions and modules/building blocks. In fact, if this occurs early enough in the manufacturing cycle, a smaller footprint, and perhaps fewer "user" layers may be achieved. This interactive process results in a faster and simpler time to use of the system on a chip (SOC).

Figure 9:
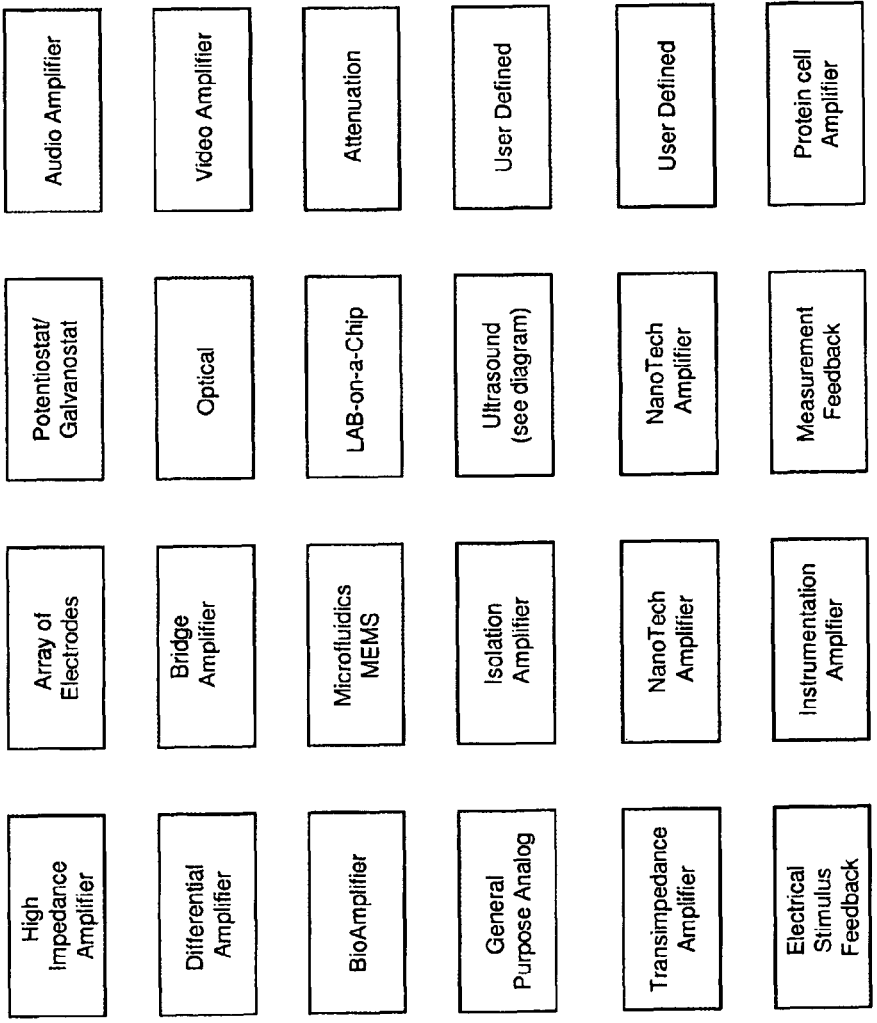
FIG. 9 illustrates various sensor interface modules in accordance with embodiments of the invention.

Referring now to FIG. 9, there are illustrated various sensor pre-amplifier interface modules or masks.

Thus, the various sensors and sensor pre-amplifier interface modules are illustrated for various embodiments of the invention. As will be clear to one practiced in this field, various of these modules can be made "standard" for a chip, while others, can be added by the user, depending upon the needs of the user.

Referring now to FIGS. 10A and 10B, there is provided a high level typical system specification for the various elements of the system on a chip and for enabling operation of this flexible module and its manufacturing construction based upon the needs described herein.

As a result, the structure and system described hereinabove enables a flexible system on a chip to be produced using both analog and digital elements in a side-by-side relationship on a single chip (or if required two or more chips, for example an analog chip and a connected digital chip) to allow both hardwired burning of connections as well as programmed connections to be made, and thus enable a single multi-layer chip structure or a multi-chip module to be easily modified for many purposes. Those purposes include various purposes described in U.S. Pat. Nos. 6,029,090 and 6,684,106 as well as all the other Herbst issued U.S. Patents Nos. 6,021,347, 6,708,066, 7,526,334, 7,517.311, and 7,160,241, U.S. pending patent application Ser. Nos. 11/063,195, 11/151,967, 11/213,050, 12/098,257, 12/431,730, 12/485,855, and 12/507,506, and International Publication No. WO 2010/065678 A1. While these relate substantially to the medical application field, that is not the only use of such a system on a chip which can be adapted for uses beyond medical applications, including, for example, a wide-range of measurement and control systems.

What is claimed is:

1. A configurable semiconductor chip module system comprising:

analog elements;

digital elements;

connection elements between said analog elements and said digital elements, wherein:

a first set of said analog elements and said digital elements receives inputs from respective sources; and a second set of said analog elements and said digital elements generates at least one of output signals for generating control signals having selected electrical and time spatial properties and outputs presenting one or more measurements based on said inputs from said first set of said analog elements and said digital elements to one or more output receiving elements; and a configuration mechanisms that automatically configures said connection elements between said analog elements and said digital elements in response to receiving at least one of: a desired input, a desired output, a desired output signal, and a desired feedback from selections entered on a user interface, said user interface is configured to execute on the configurable semiconductor chip module system and wherein said user interface is a graphical user interface that allows a non-technical user to input commands to the chip module and functionally control operation of said chip module, said connection elements being configurable after creation of said analog elements and said digital elements.

2. The chip module system of claim 1 wherein said chip module system comprises a single chip module.

3. The chip module system of claim 1 wherein said chip module system comprises:

a plurality of predetermined mask layers and a plurality of custom configurable mask layers, wherein the user can custom design desirable functions in said plurality of custom configurable mask layers.

4. The chip module system of claim 3 wherein:

said plurality of custom configurable mask layers are laid on top of a flexible, predefined, functional structure.

5. The chip module system of claim 1 wherein said analog elements and said digital elements comprise at least one of:
- a sensor interface and conditioning module;
- a multi-functional electrical stimulator output module;
- a processor and memory module; and
- a control module.

6. The chip module system of claim 5 wherein said analog elements and said digital elements further comprise:
- a communications interface module for receiving and sending wireless communications.

7. The chip module system of claim 1 wherein said second set of said analog elements and said digital elements further comprise:
- elements responsive to input sensor signals;
- elements responsive to user control signals from a graphical user interface and from processing elements;
- wherein the output signal generated for application to a stimulation receptor is created based upon said sensor inputs, said user control signals, and a configuration of said processing elements.

8. A configurable semiconductor chip module for use in patient treatment comprising
- analog elements;
- digital elements;
- connection elements between said analog elements and said digital elements, wherein:
  - a first set of said analog elements and said digital elements receives analog and digital inputs from respective sources; and
  - a second set of said analog elements and said digital elements generates at least one of output signals for generating control signals having selected electrical and time spatial properties and outputs presenting one or more measurements useful in medical treatment based on said inputs from said first set of said analog elements and said digital elements to one or more output receiving elements; and
- a configuration mechanism that automatically configures said connection elements between said analog elements and said digital elements in response to receiving at least one of: a desired input, a desired output, a desired output signal, and a desired feedback from selections entered on a user interface, said user interface is configured to execute on the configurable semiconductor chip module and wherein said user interface is a graphical user interface that allows a non-technical user to input commands to said chip module and functionally control operation of said chip module, said connection elements being configurable after creation of said analog elements and said digital elements.

9. The chip module of claim 8 wherein said chip module comprises:
- a plurality of predetermined mask layers and a plurality of custom configurable mask layers, wherein the user can custom design desirable function in the plurality of custom mask layers.

10. The chip module of claim 9 wherein:
- said plurality of custom configurable mask layers are laid on top of a flexible, predefined, functional structure.

11. The chip module of claim 8 wherein said analog elements and said digital elements further comprise:
- a communications interface module for receiving and sending wireless communications from and to sensors monitoring bodily parameters.

12. The chip module of claim 8 wherein said second set of said analog elements and said digital elements further comprise:
- elements responsive to input sensor signals;
- elements responsive to user control signals from a graphical user interface and from processing elements;
- wherein the output signal generated for application to a stimulation receptor, is created based upon said sensor inputs, said user control signals, and a configuration of said processing elements.

13. A passive configurable semiconductor chip module for use in making measurements of parameters relating to status of patients comprising:
- analog elements;
- digital elements;
- connection elements between said analog elements and said digital elements, wherein:
  - a first set of said analog elements and said digital elements receives analog and digital inputs from respective analog sensors; and
  - a second set of said analog elements and said digital elements generates at least one of output signals for generating control signals having selected electrical and time spatial properties and outputs presenting one or more measurements based on said inputs from said first set of said analog elements and said digital elements to one or more output receiving elements; and
- a configuration mechanism that automatically configures said connection elements between said analog elements and said digital elements in response to receiving at least one of: a desired input, a desired output, a desired output signal, and a desired feedback from selections entered on a user interface, said user interface is configured to execute on the configurable semiconductor chip module and wherein said user interface is a graphical user interface that allows a non-technical user to input commands to said chip module and functionally control operation of said chip module, said connection elements being configurable after creation of said analog elements and said digital elements.

14. The chip module of claim 13 wherein said chip module comprises:
- a plurality of predetermined mask layers and a plurality of custom configurable mask layers, wherein the user can custom design desirable function in the plurality of custom mask layers.

15. The chip module of claim 14 wherein:
- said plurality of custom configurable mask layers are laid on top of a flexible, predefined, functional structure.

16. A method of manufacturing a flexibly configurable semiconductor chip module for receiving and outputting various signals not specifically known at the time of manufacturing, comprising:
- providing a plurality of analog elements, digital elements, and connection elements between said analog elements and said digital elements, wherein:
  - a first set of said analog elements and said digital elements is configured to receive inputs from respective sources; and
  - a second set of said analog elements and said digital elements is configured to generate at least one of output signals for generating control signals having selected electrical and time spatial properties and outputs presenting one or more measurements based on said inputs from said first set of said analog elements and said digital elements to one or more output receiving elements; and
- providing a configuration mechanism, using a processor, that automatically configures said connection elements between said analog elements and said digital elements in response to receiving at least one of: a desired input, a desired output, a desired output signal, and a desired feedback from selections entered on a user interface, said user interface is configured to execute on the configurable semiconductor chip module system and wherein said user interface is a graphical user interface that allows a non-technical user to input commands to said chip module and functionally control operation of said chip module, wherein said connection elements are configured after creation of said analog elements and said digital elements to configure the module.

17. The method of claim 16 comprising:
laying a plurality of predetermined layers and a plurality of custom configurable layers on a substrate; and
enabling a user to custom design desirable function in the plurality of custom layers.

18. The method of claim 17 comprising:
laying said plurality of custom configurable layers on top of a flexible, predefined, functional multi-layer structure.

* * * * *